US008818509B2

(12) United States Patent
Weiss (10) Patent No.: US 8,818,509 B2
(45) Date of Patent: Aug. 26, 2014

(54) IMPLANTABLE ELEMENT AND ELECTRONIC IMPLANT

(75) Inventor: Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 548 days.

(21) Appl. No.: 13/006,501

(22) Filed: Jan. 14, 2011

(65) Prior Publication Data

US 2011/0196460 A1 Aug. 11, 2011

Related U.S. Application Data

(60) Provisional application No. 61/316,876, filed on Mar. 24, 2010.

(30) Foreign Application Priority Data

Feb. 11, 2010 (DE) .......................... 10 2010 000 373

(51) Int. Cl.
*A61N 1/05* (2006.01)
*A61N 1/08* (2006.01)

(52) U.S. Cl.
CPC ... *A61N 1/05* (2013.01); *A61N 1/08* (2013.01)
USPC .............. 607/20; 607/116; 607/119; 607/122

(58) Field of Classification Search
USPC ................................. 607/116, 119, 122, 20
See application file for complete search history.

(56) References Cited

U.S. PATENT DOCUMENTS 5,651,767 A * 7/1997 Schulman et al. ................. 604/8
7,363,090 B2 4/2008 Halperin
2005/0222658 A1 * 10/2005 Hoegh et al. .................. 607/116
2008/0051854 A1 * 2/2008 Bulkes et al. .................... 607/60
2008/0132985 A1 * 6/2008 Wedan et al. ................. 607/122
2009/0099555 A1 4/2009 Viohl et al.
2009/0105789 A1 4/2009 Olsen
2009/0171421 A1 7/2009 Atalar
2009/0198314 A1 8/2009 Foster
2009/0270956 A1 10/2009 Vase et al.

FOREIGN PATENT DOCUMENTS

WO WO2009049310 4/2009

OTHER PUBLICATIONS

"Dimensioning." The Free Dictionary. Farlex, Inc., n.d. Web. Jan. 30, 2013. <http://www.thefreedictionary.com/dimensioning>.*
"The Inductor." Electronics-Tutorials.ws. Electronics-Tutorials.ws,, n.d. Web. Jan. 30, 2013. <http://www.electronics-tutorials.ws/inductor/inductor.html>.*
European Search Report dated Jan. 5, 2012 (8 pages).

* cited by examiner

*Primary Examiner* — Niketa Patel
*Assistant Examiner* — Christopher A Flory
(74) *Attorney, Agent, or Firm* — ARC IP Law, PC; Joseph J. Mayo (57) ABSTRACT

Implantable element having an elongate main body, a functional conductor which extends in the longitudinal direction of the main body or forms it, and which acts to implement a medical function of the element and has an inductive section, and magnetic flux generation means for generating a magnetic flux in the surroundings of the functional conductor, in particular of its inductive section, which are magnetically coupled to the functional conductor in such a way that the magnetic flux generated upon a current flux through the functional conductor is counteracted and the current flux density through the functional conductor is thus reduced.

14 Claims, 9 Drawing Sheets

IMPLANTABLE ELEMENT AND ELECTRONIC IMPLANT

This application claims the benefit of U.S. Provisional Patent Application 61/316,876, filed on 24 Mar. 2010, and also takes priority from German Patent Application DE 10 2010 000 373.5, filed 11 Feb. 2010, the specifications of which are both hereby incorporated herein by reference.

BACKGROUND OF THE INVENTION

1. Field of the Invention

The invention relates to an implantable implant having an elongate main body and a functional conductor extending in the longitudinal direction of the main body, which acts to implement a medical function of the element. Elements of this type are in particular stimulation electrode lines (sometimes also referred to in short as "electrodes") of cardiac pacemakers or shock electrode lines of implantable defibrillators, but also catheters which contain an elongate conductive structure, or also guide wires or vascular supports (stents), in which the main body itself represents the functional conductor in the meaning of the terminology of this patent application. Furthermore, the invention relates to an electronic implant, which is typically inserted into the body using a line.

2. Description of the Related Art

Medical implants such as the listed pacemakers and defibrillators frequently have an electrical connection to the interior of the body of the patient. Such a connection is used to measure electrical signals and/or to stimulate body cells. This connection is often implemented as an oblong electrode. In the present case, electrical signals are transmitted between the implant and the electrode contacts (tips, rings, HV shock coils, sensors, inter alia) using materials having good electrical conduction.

If a system made of implant and electrode is subjected to strong interfering field (EMI, MRI), undesired misbehavior may occur, especially heating of parts of the system or electrical malfunctions (e.g., resets).

The cause of the undesired misbehavior is the interaction of the field with the oblong line structure, which forms an inductance: It acts as an antenna and receives energy from the surrounding fields. The antennae can discharge this energy on the therapeutically used lines distally to the tissue via the electrode contacts (tip, ring . . . ) or proximally to the implant.

Comparable problems also occur in other oblong conductive structures, whose proximal end is not necessarily connected to an implant (e.g., in catheters, guide wires, temporary electrodes, stents, etc.).

In recent years, countermeasures to solve the described problems have already been proposed. In addition to measures for shielding the RF energy from the electrode or the introduction of a bandpass filter into the electrode feed line (cf. U.S. Pat. No. 7,363,090 B2) a thermoswitch in the electrode feed line is also known; cf. US2009/0105789. In addition to unfavorable design properties (rigidity of the electrode), such a thermoswitch also has the disadvantages of significant hysteresis and a poorly settable and controllable temperature range and can only turn the electrode tips on or off completely, so that in the turned-off state, stimulation or derivation of signals is no longer possible. The application of this electrode for pacemaker-dependent patients is thus precluded.

The solutions from, for example, U.S. Pat. No. 7,363,090 B2 do allow a continuous electrical path to be provided for low frequencies (i.e., for the typical pacemaker function of pacing and sensing), but they are rigid in their embodiment known up to this point and impair the control capability of the electrodes significantly during implantation, so that the clinical use is put into question de facto. These known solution variants also require additional contact points not required in the typical production process of an electrode, in order to install this solution, which is implemented as a discrete element. This introduces additional risk points into the design of such an electrode.

Further approaches for solving the above-described problems are described in US 2009/0198314, which discloses suitable dimensioning and a coaxial multicore construction of a pacemaker electrode line, and in US 2009/0171421, which teaches the installation of a plurality of circuit segments spaced apart from one another having high impedance in an electrode line having coiled functional conductor. In addition, reference is made to WO 2009/049310 A1, in which multi-core conductor configurations having coaxial construction or elongate conductors in parallel configuration are also proposed as a configuration for suppressing the alternating current propagation along elongate implants.

BRIEF SUMMARY OF THE INVENTION

Embodiments of the invention are based on the object of providing an improved implantable line of the described type, which has improved properties in strong external fields. Furthermore, an electronic implant having reduced vulnerability to interference in external fields is to be provided.

This object is achieved by an implantable element having the features as claimed herein. Expedient refinements of the idea of embodiments of the invention are also the subject matter of the claims.

In one embodiment of the invention, it is provided that the magnetic flux generation means have an inductively acting conductor section, which is incorporated without interruption of the course of the functional conductor in the main body or is placed thereon, and a capacitive element attached thereto to form an LC element.

In a further embodiment, the implantable element is implemented as an electrode line having at least one electrode and one electrode terminal contact on one end of the line, the functional conductor connecting the electrode to the electrode terminal contact and having at least one coiled section, and the current flux generation means having a flux generation section coiled coaxially or corradially with the coiled section of the functional conductor.

In an alternative embodiment thereto, the implantable element is implemented as a guide wire or catheter or vascular support, the functional conductor in particular having at least one coiled section and the current flux generation means having a flux generation section coiled coaxially or corradially with the coiled section of the functional conductor.

One design of both variants provides that the magnetic flux generation means comprise multiple flux generation sections connected one behind another along the functional conductor.

In a further embodiment of the invention, it is provided that the magnetic flux generation means have a capacitive element, which is embedded in an inner chamber of the inductive section of the functional conductor or at least partially encloses the inductive section. For this purpose, the capacitive element, which is embedded in the inductive section or at least partially encloses it, is formed by two coaxial metal cylinders having the dielectric filling. It is still more specially provided that multiple capacitive elements are situated one behind another along the functional conductor.

A further embodiment of the implantable element according to the invention is distinguished in that the magnetic flux generation means have multiple components which are adapted to various frequencies of an external field by dimensioning of the particular inductance and/or capacitance. In particular, the components of the magnetic flux generation means which are adapted to various frequencies are formed for this purpose by inductive sections, which are situated one behind another along the functional conductor, having embedded or enclosing capacitive elements, which have various values of the inductance and/or capacitance.

A further embodiment is designed in such a way that the or at least one flux generation section of the magnetic flux generation means is implemented as a conductive coating of the functional conductor, in particular of its inductive section.

In a further embodiment, the implantable element is provided with mechanical adjustment means for changing the relative position between the inductive section of the functional conductor and or the one flux generation section of the magnetic flux generation means.

A design which is advantageously adaptable to various application situations is distinguished in that the magnetic flux generation means are settable to a predetermined active frequency, in particular in the implanted state of the element.

The means according to the invention may be incorporated in an electrode and exert their function, without the conductor to be influenced having to be interrupted. The reliability of an electrode designed in this way is not impaired by additional contact points (as in the case of known solutions).

The means may, with suitable design, be integrated into the electrode line so that a coaxial inner lumen remains, through which a mandrin can pass. The control capability of such an electrode thus remains unimpaired (in contrast to a known solution).

The means may be divided into segments. A longer rigid section thus does not result.

The means may be implemented with the aid of the external coil, which is coaxially located in any case, or at least sections of this coil can be used.

A breakdown of the means according to the invention only results in the loss of the MR safety, and does not compromise the therapeutic purpose, e.g., as a stimulation electrode.

The solution is also transferable to electrodes having non-coiled conductors, in that their conductors (e.g., cables) are only formed into a helix in sections (inductive section), but without interrupting them.

The means according to the invention may be implemented so that they may be installed later on standard electrodes (i.e., these electrodes may be retrofitted).

The following features are provided in special embodiments of the invention:
1. The conductor to be inductively influenced is a conductor inside the implant housing/electronics.
2. The functional conductor to be inductively influenced is a (long>5 cm) stent.
3. The conductor to be inductively influenced is a (long>5 cm) orthopedic implant (electrically conductive).
4. The conductor to be inductively influenced is located outside the implant housing, in particular it is an electrode feed line of an IPG.
5. The device for generating the magnetic flux (or counter flux) is a resonant circuit.
6. The quality of the resonant circuit is set so that the impedance absolute value of the conductor element, whose magnetic flux is thus influenced, is greater than 200'Ω.
7. The resonant circuit is especially a passive LC resonant circuit; in general it consists of an inductive element and a capacitive element, which can each also be implemented by spatially distributed material properties.
8. The resonant circuit is a parallel resonant circuit.
9. The inductive element of the resonant circuit is magnetically coupled to the described electrical conductor, in particular to its inductive section (or element).
10. A pronounced inductive section is implemented at least locally by geometrical shaping of the described electrical conductor, in particular designed for the purpose of being coupled to the inductive element of the resonant circuit.
11. The inductive section is implemented by a coil or primary coil of a transformer incorporated in series in the line.
12. The inductive section is generated by geometrical shaping of the conductor, in particular in helix form or in planar coil form, without the conductor being interrupted and an additional component being interposed using contacting technology.
13. The inductive element of the resonant circuit is the geometrical counterpart of the inductive conductor section, especially the secondary coil of the transformer, because the maximum coupling is generated. The coupling factor is preferably k>0.5.
14. The coupling direction is such that the current flow is reduced in the described electrical conductor.
15. The resonant frequency of the resonant circuit is adapted so that currents in the described electrical conductors are only selectively suppressed with respect to the desired frequency.
16. One application provides suppressing narrow-band interfering signals within a bandwidth of <10 MHz in particular.
17. The inductive element/section is a solenoid coil, which is situated coaxially or corradially to the electrode feed line (which is coiled in this case and/or locally coiled for this purpose).
18. The inductive element/section is a flat coil.
19. The inductive elements/sections are implemented as mechanically flexible.
20. The inductive elements/sections allow a cavity (the device can be integrated into the electrode line so that a coaxial inner lumen remains, through which a mandrin can pass. The control capability of such an electrode thus remains unimpaired).
21. The capacitor of the resonant circuit is implemented coaxially around the inductive element.
22. The capacitor is mechanically flexible.
23. The inductive element/section (in particular that of the resonant circuit) has a series resistance r<0.05'Ω per turn.
24. The capacitor (the capacitive element) has an ESR<0.05'Ω, the dielectric material used has a relative permittivity>8.
25. The resonant circuit can also have at least one electrical contact to the described electrical conductor, but without having to interrupt it.
26. The means according to the invention may be connected one behind another multiple times and distributed over the conductor length.
27. The frequencies to be suppressed are >1 MHz.
28. Means may be implemented for various frequencies and connected one behind another within the same implant/conductor, so that protection against all of these frequencies exists simultaneously.
29. The inductive element of the resonant circuit is wound between the turns of a coiled line (coaxially or corradially).
30. The inductive element of the resonant circuit is implemented as a highly conductive coating on the inductive element of the described conductor, especially coiled as a wire around the conductor (which can be coiled around itself—as in musical instrument strings).
31. The inductive element of the conductor is a section of the coiled electrode feed line itself.
32. The length of the inductive element is <=1 cm.
33. The inductive elements are implemented from multicore leads.
34. The capacitive element is implemented by a dielectric material, which is introduced between the turns of the inductive element.
35. The means according to the invention are implemented as an element which can be installed later on a typical line (in particular an IPG electrode) (standard electrodes can thus be retrofitted).
36. The means according to the invention are implemented with the aid of the coaxially located external coil (sectionally) of a multipolar electrode.
37. The means (implemented as an electrically active device) feed in a generated signal, in order to generate the counter flux; the implant/the electrode is equipped with a corresponding generator.
38. The resonant circuit contains active (battery-operated) elements to increase the quality.
39. The tube coils of a transmitter (L, L1) formed between the functional coil and the additional inductor are mechanically mobile, so that L mechanically implements a pitch transducer.
40. The section of L1 is coated with a highly electrically conductive layer over at least the length of the possible translational movement, the turns not touching one another in this section, however.
41. L (screw) is implemented coaxially over L1 (nut), so that a screw-nut connection is implemented.
42. There can be electrical contact between the turns of the screw and the nut, it is movable in the meaning of a slip contact.
43. Both the turns of the screw (L1) and also the grooves of the nut (L) are highly electrically conductive over the translational length. The conductivity of this coating is preferably greater than 2× higher than that of the coil (electrode feed line).
44. The means are adjustable with respect to the resonant frequency (active frequency of the signal barrier).
45. The adjustment can be performed in the implanted state.
46. The adjustment is performed by trimming of the capacitor (e.g., voltage-dependent capacitance).
47. The adjustment is performed automatically as a function of the interfering frequency (i.e., the implant automatically adapts the protective action to the operating frequency of an MRI scanner, for example).
48. The adjustment is performed via a signal which is generated by the implant.
49. The implant is externally programmable to generate such a signal.

BRIEF DESCRIPTION OF THE DRAWINGS

Advantages and expedient features of the invention also result from the following description of special embodiments and/or of their calculation bases on the basis of the figures. In the figures.

DETAILED DESCRIPTION OF THE INVENTION

Figure 1:
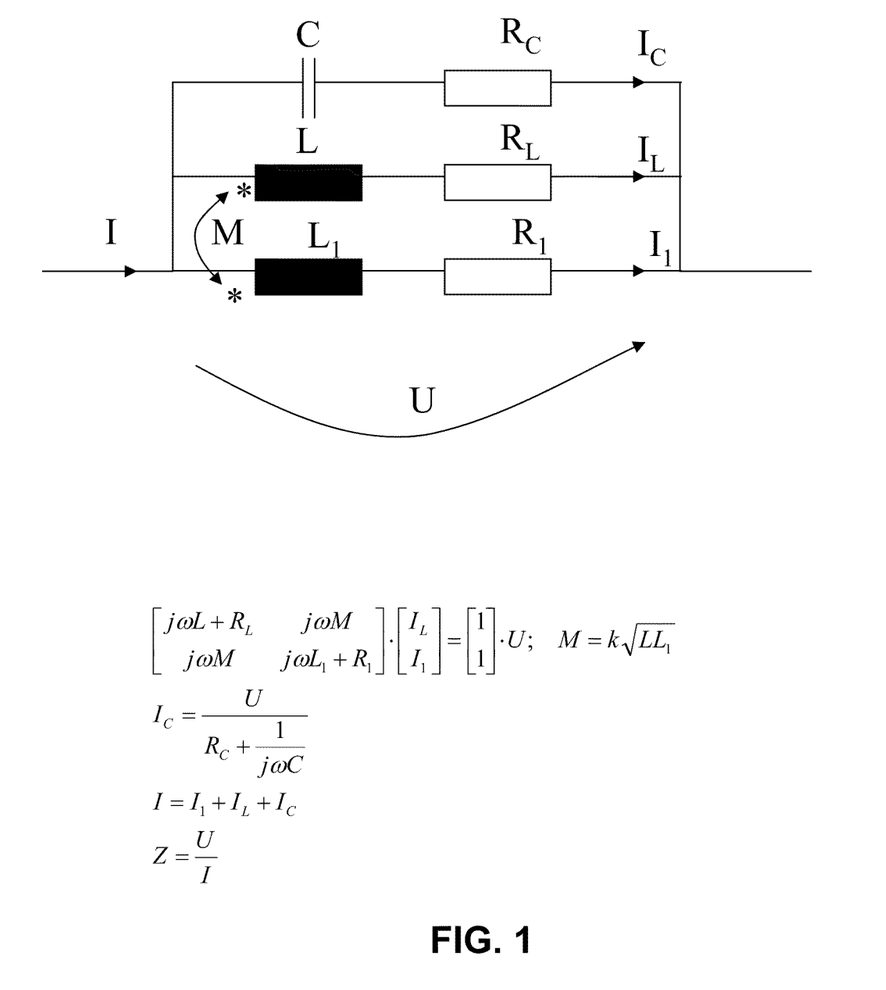
FIG. 1 shows an equivalent circuit diagram to explain a first embodiment of the invention with associated calculation bases.
Figure 2:
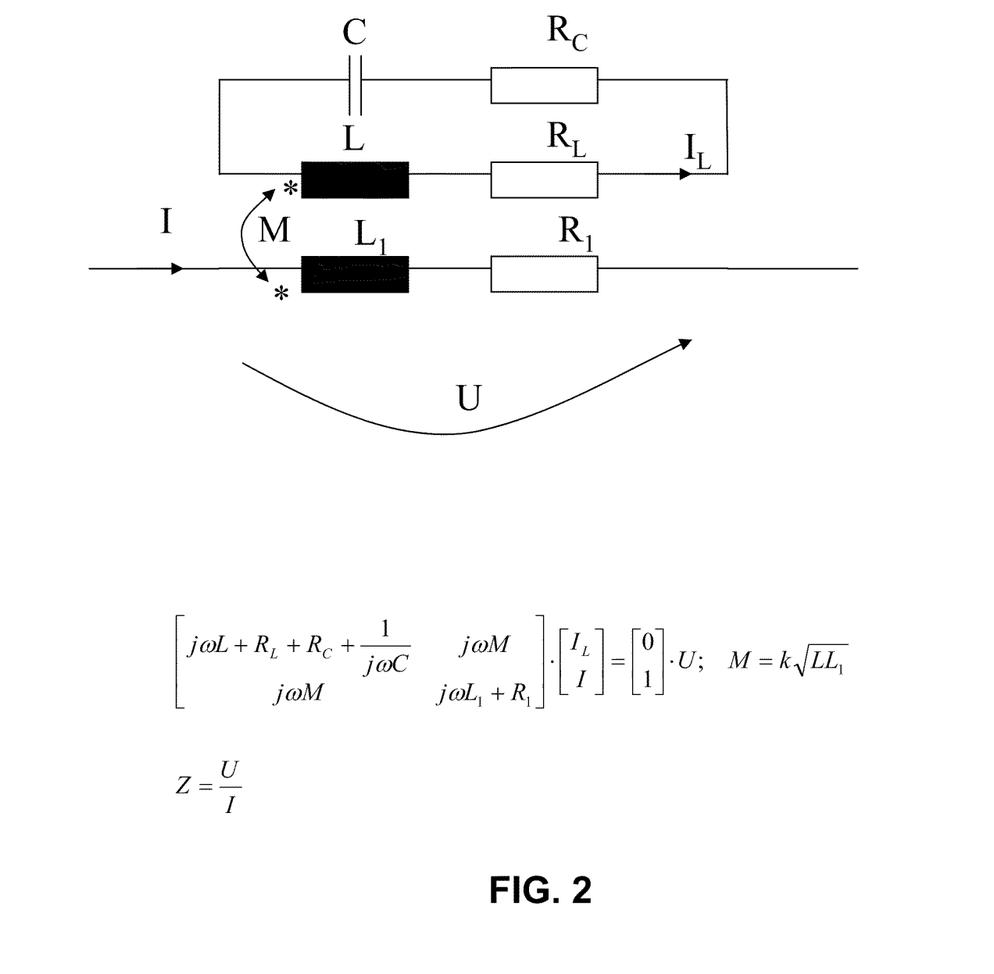
FIG. 2 shows equivalent circuit diagram to explain a first embodiment of the invention with associated calculation bases.

FIGS. 1 and 2 show, each in the form of an equivalent circuit diagram with associated calculation bases, illustrations to explain the principle according to the invention in two embodiments. R1 and L1 designate an Ohmic resistor and an inductor of a functional conductor, and L and C designate the inductance and capacitance, respectively, and RL and RC designate the corresponding loss resistances of an LC resonant circuit, which is used as the magnetic flux generation means to build up a magnetic flux, which can be coupled into the functional conductor to reduce the current flux built up therein by an external field. The LC resonant circuit is adapted on the foundation of the equations disclosed in the figures to the field frequency (or a frequency band) to be suppressed in the implant, in order to maximize the absolute value of the magnetic flux (counter flux).

Figure 3:
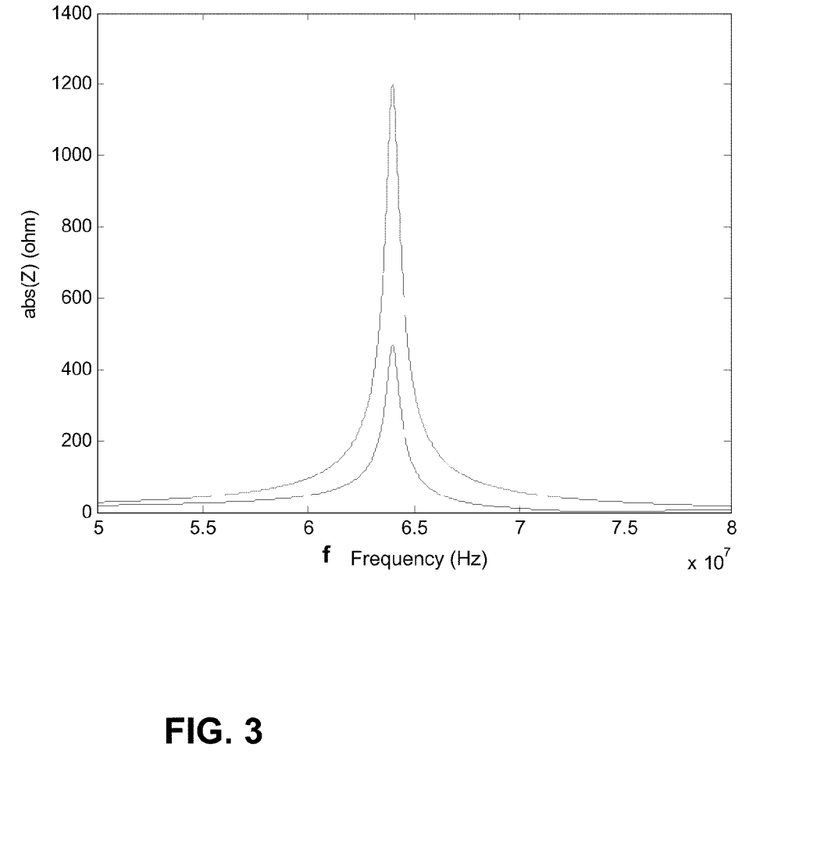
FIG. 3 shows a graphic view to illustrate the impedance slope, which an inductive element causes in an embodiment of the invention by inductive coupling of the magnetic flux barrier, with associated calculation bases.

FIG. 3 shows the results of a calculation (simulation) of the frequency-dependent impedance increase, which the inductive section of the functional conductor causes solely because of the inductive coupling with the magnetic flux generation means (the "magnetic flux barrier"). The calculation parameters are as follows:

$r=0.5e-3$; % coil radius (m)

$l=0.5e-2$; % coil length (m)

$n=3$; % turns per m $Rc=0.02$; % ESR of the capacitance ESR=0.02 ohm@64 MHz $rl=0.01$; % resistance of resonator coil per turn (ohm)

$rl1=30/0.6$; % spiral resistance per m coil (ohm)

$k=0.8$; % coupling factor (curve having higher maximum)

$k=0.5$; % coupling factor (curve having lower maximum)

The desired capacitance value C is calculated therefrom according to FIG. 1 or FIG. 2.

Figure 4A:
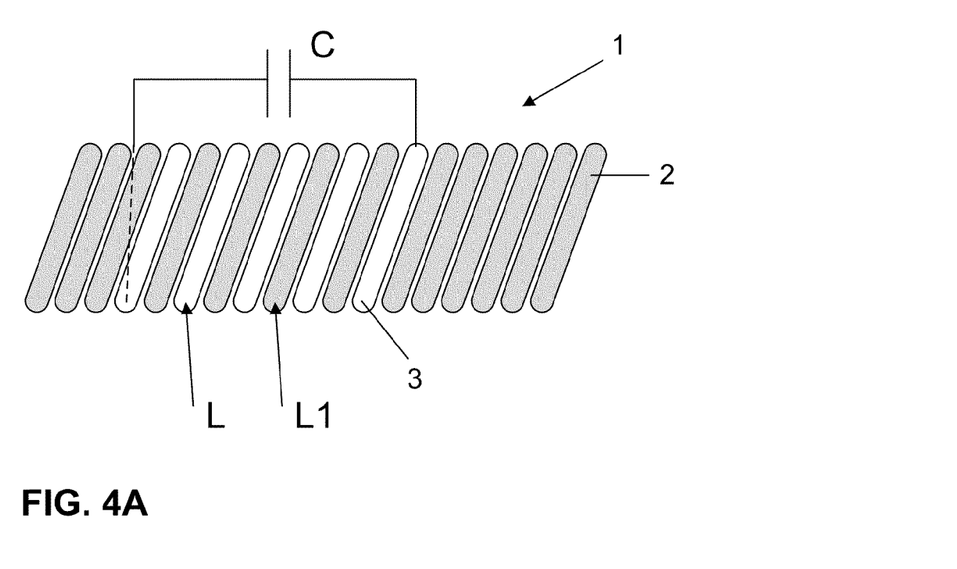
FIGS. 4A and 4B show schematic views of the conductor structure of a line according to the invention (FIG. 4B having exemplary embodiment of a capacitor component)
Figure 4B:
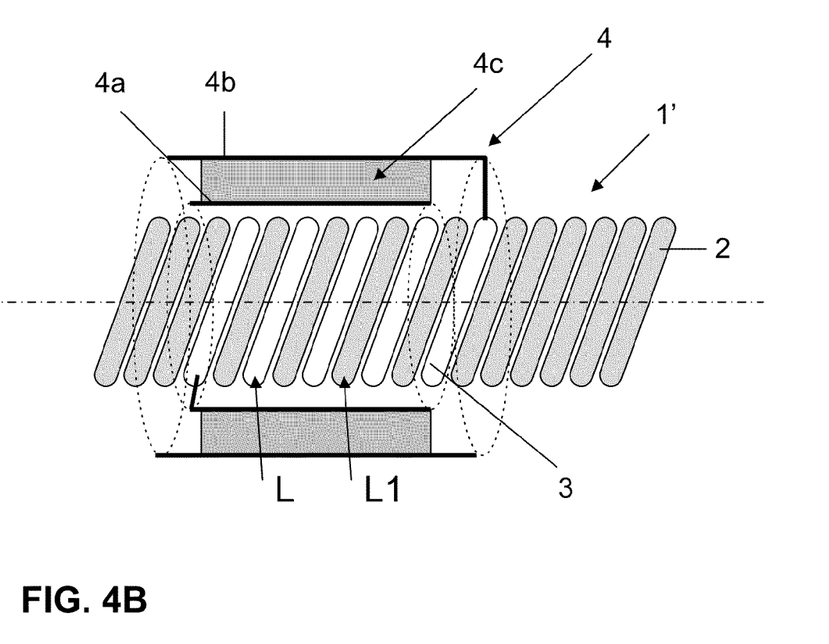

FIG. 4A schematically shows the design construction of the interior of an electrode line 1, which comprises a coiled functional conductor 2, which has an inductance L1 in one section and in which a further conductor 3 having an inductance L is wound corradially, at equal diameter and equal pitch, with which a capacitance C is associated. FIG. 4B shows that the capacitance C can be implemented by a capacitor 4 enclosing the electrode coil 2 and/or 3, which is constructed from two concentric metal cylinders 4a, 4b having a dielectric material 4c situated between them. In order to achieve the capacitance in the pF range, which is required in the event of typical interfering fields, dielectric materials having a relative dielectric constant (DK)>8 may be used with respect to realistic dimensions of the magnetic flux generation section.

Figure 5:
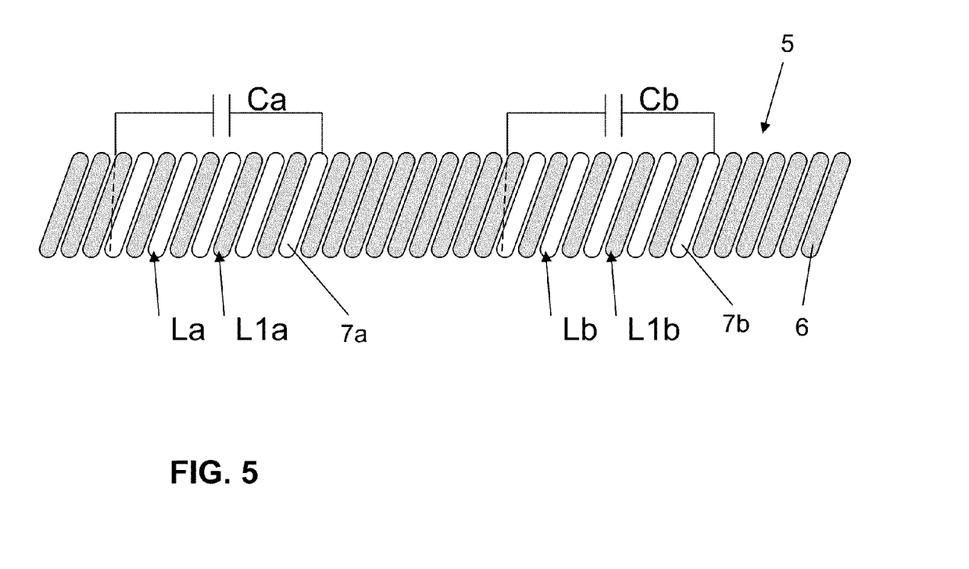
FIG. 5 shows a schematic view of the conductor structure of a further line according to the invention.

FIG. 5 shows, as a further embodiment, the electrode coil of a further electrode line 5, in which, as in the embodiment according to FIGS. 4A and 4B, magnetic flux generation means are fitted corradially into a functional coil 6. However, in this embodiment, in two inductive sections L1a and L1b of the functional coil 6, a first additional coil section 7a having an inductance La, with which a capacitance Ca is associated, and a second additional coil section 7d having an inductance Lb, with which a capacitance Cb is associated, are inserted. In this way, two magnetic flux barriers which can be adapted separately to different frequencies are formed in the electrode line. Independently thereof, the configuration of individual magnetic flux generation means distributed over the length of a functional conductor can have advantages with respect to the mechanical properties of the implant provider, in particular greater flexibility.

Figure 6:
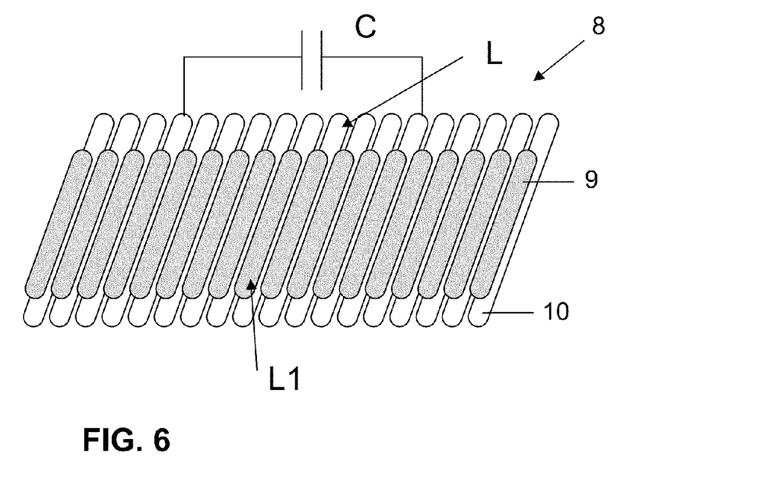
FIG. 6 shows a schematic view of the conductor structure of a further line according to the invention.

FIG. 6 shows, as a further embodiment, an electrode line 8 having a coiled functional conductor 9 and a further coiled section 10, situated coaxially thereto and enclosing the functional conductor 9, having an inductance L and an associated capacitance C. Moreover, in the coaxial embodiment, the winding direction of the coil of the magnetic flux generation means can also be opposite to the winding direction of the functional conductor.

Figure 7:
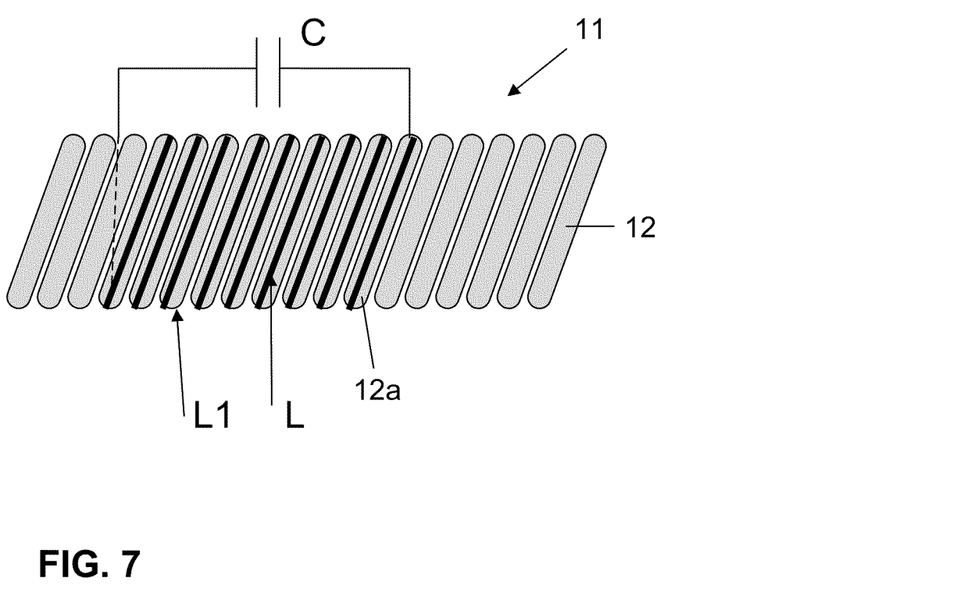
FIG. 7 shows a schematic view of the conductor structure of a further line according to the invention.

FIG. 7 shows, as a further embodiment of the invention having a particularly simple design, an electrode line 11, in which the functional conductor 12 is provided in a section with an inductance L1 having a coating 12a, which implements the inductance L of a resonant circuit formed using the capacitance C as the magnetic flux generation means. The coating is applied here to the functional conductor in the form of two semicylindrical sections.

Figure 8:
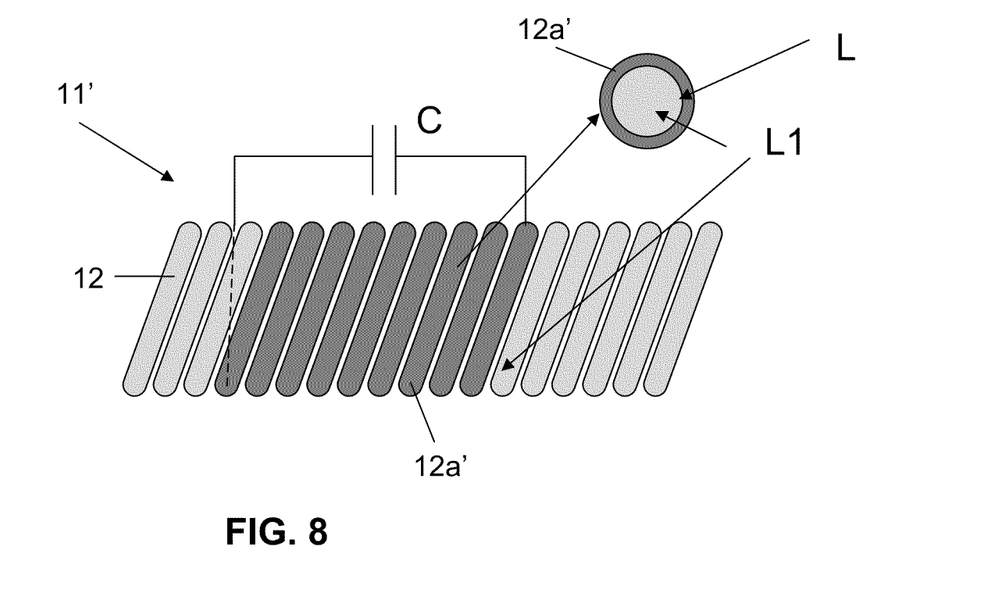
FIG. 8 shows a schematic view of the conductor structure of a further line according to the invention.

FIG. 8 shows, as an alteration, an electrode line 11', in which the functional conductor 12 is provided in the relevant section with a coating 12a' enclosing the entire conductor circumference.

Figure 9:
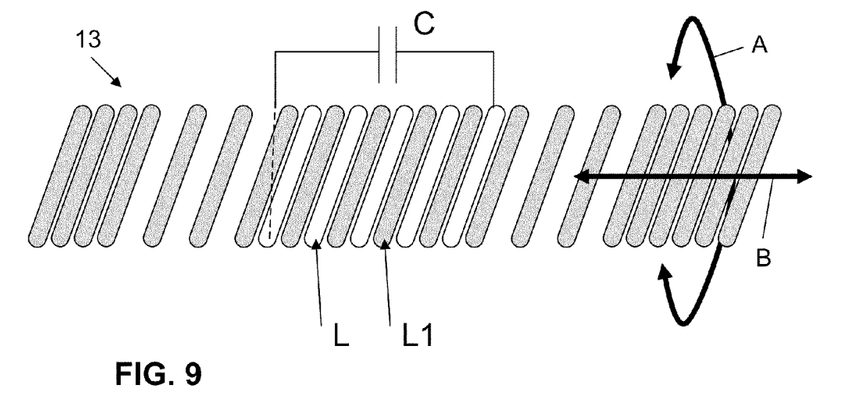
FIG. 9 shows a schematic view of the conductor structure of a further line according to the invention.

In FIG. 9, as a further embodiment, the internal structure of an electrode line 13 is schematically shown, the arrows A, B symbolizing a mechanical mobility of the magnetic flux generation means in relation to the functional conductor or, more precisely, the particular coil sections associated with these elements. In this way, a pitch transducer can be mechanically implemented. In particular, the mobility can be implemented like a screw-nut relationship between the coil sections, in that the inductive element L engages like a nut in the functional conductor L1. The capacitive element is only shown symbolically. It is advantageous if the functional conductor L1 is moved in relation to L.

Figure 10:
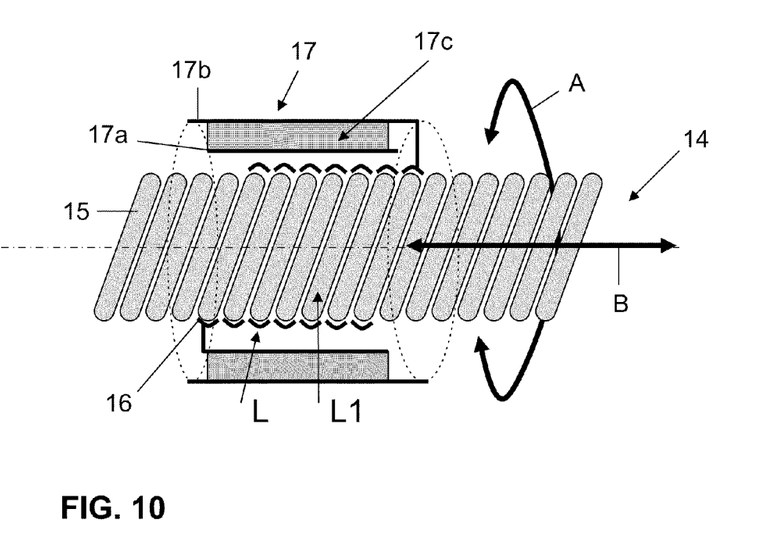
FIG. 10 shows a schematic view of the conductor structure of a further line according to the invention.

FIG. 10 shows, as an alteration of this embodiment, an electrode line 14, in which the functional conductor 15 is movable like a screw in a thread of a nut. The internal thread is formed by a conductive structure 16, the turns each having no lateral contact to one another. As in the embodiment according to FIG. 4B, a resonant circuit capacitor 17, which sheathes the relevant section of the functional conductor 15, is provided with an internal cylinder 17a, an external cylinder 17b, and a dielectric material 17c, which is attached to the inductive element 16 of the resonant circuit of the functional conductor.

Figure 11:
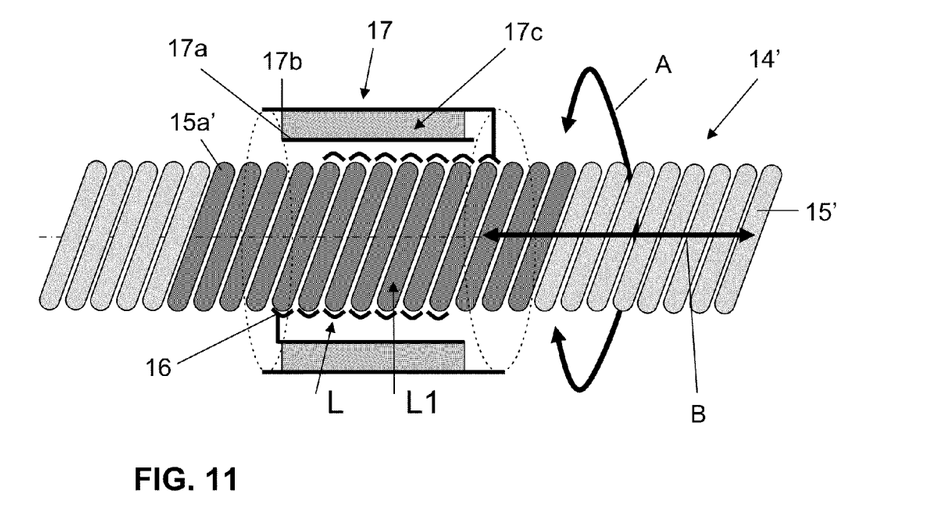
FIG. 11 shows a schematic view of the conductor structure of a further line according to the invention.

FIG. 11 shows, as a further modification, the interior of an electrode line 14', in which the functional conductor 15' is implemented in the screw-nut translation section as a coil section 15a' having high electrical conductivity, like the "thread section" 16 of the magnetic flux generation means. The conductivity of the area designated in the present case as highly conductive is preferably to be more than twice as high as that of the functional conductor, i.e., the actual electrode coil. Alternatively, the functional conductor L itself can also be highly conductive.

Figure 12:
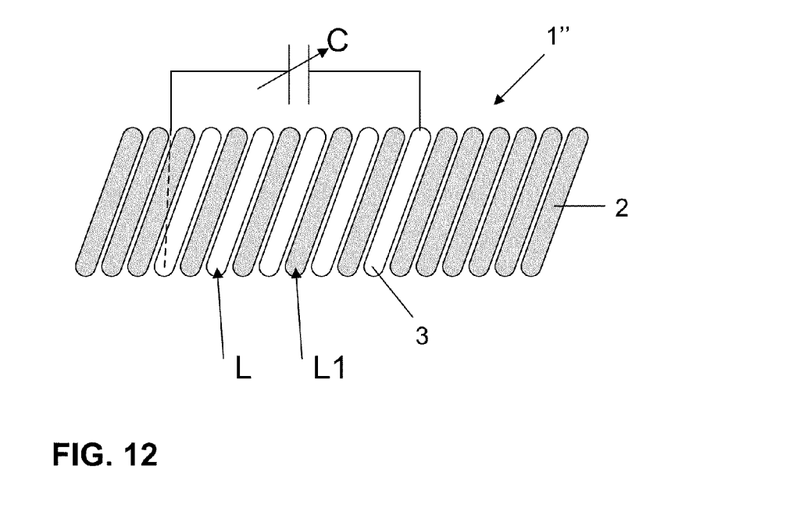
FIG. 12 shows a schematic view of the action principle of a further embodiment.

FIG. 12 shows, in a schematic sketch oriented to FIG. 4A, an electrode line 1" as a further embodiment, which has the same design features as the electrode line 1 according to FIG. 4A. However, the capacitor C of the LC resonant circuit (the magnetic flux generation means) is settable in its capacitance here, for example, voltage-controlled, in order to set the action frequency of the interfering signal reduction caused using the magnetic flux generation means. In a preferred embodiment, the adjustment, i.e., the trimming of the capacitor C, occurs automatically as a function of the interfering frequency.

Figure 13:
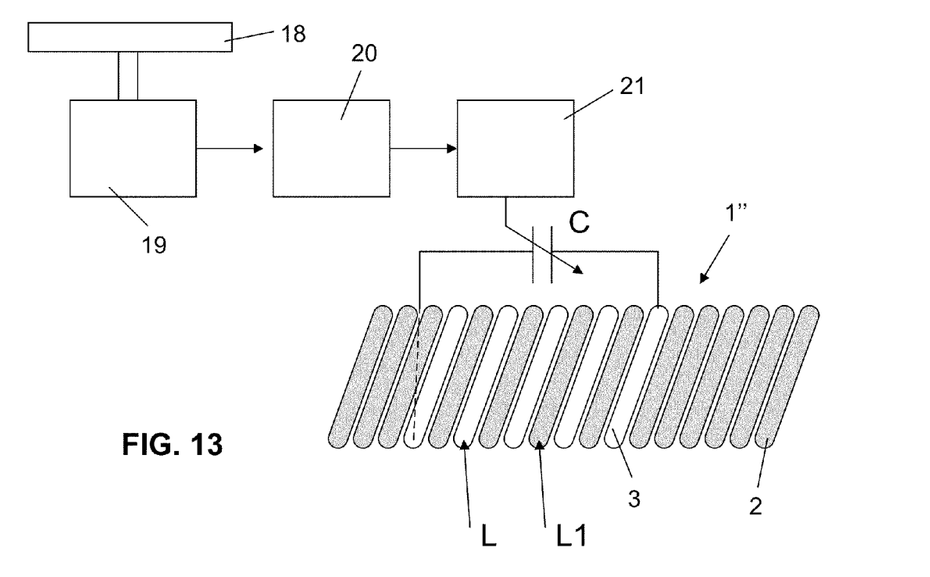
FIG. 13 shows a schematic view of the action principle of a further embodiment.
Figure 14:
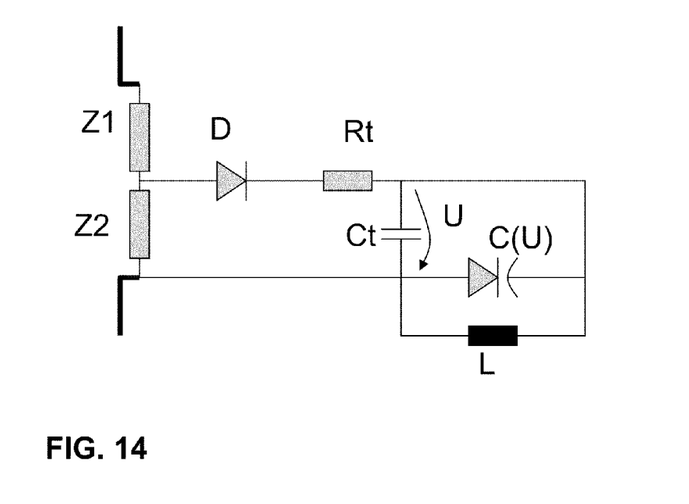
FIG. 14 shows an equivalent circuit diagram to explain the last-mentioned embodiment.

FIG. 13 shows a concrete implementation of this automatic adjustment of the magnetic flux generation means on the example of the electrode line 1" from FIG. 12. The configuration shown comprises a field sensor 18 (such as a dipole), a frequency-voltage transducer 19 connected at the input thereto, a demodulator 20 connected at the input thereto, and finally a low-pass filter 21, with whose output signal the capacitance of the capacitor C is controlled. A voltage divider made of two impedances, such as one resistor and one inductance, implements the frequency-voltage transducer in particular. The demodulator 20 can be implemented by a diode, and a reasonable implementation of the low-pass filter is an RC element. The voltage-dependent capacitor itself can be a capacitance diode (varicap, varactor), for example. FIG. 14 shows a corresponding embodiment, the impedances Z1, Z2 implementing the frequency-voltage transducer 19, the diode D implementing the demodulator 20, and Rt, Ct implementing the low-pass filter 21 from FIG. 13. The characteristic curve of the voltage-dependent capacitance is selected so that the active frequency precisely follows the frequencies of the external interfering field acquired using the field sensor 18. Alternatively, the frequency-voltage transducer can also be implemented having a corresponding compensating characteristic curve.

The implementation of the invention is not restricted to the above-described examples and emphasized aspects, but rather is also possible in manifold alterations, which are within the scope of typical measures of one skilled in the art.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable element configured to implement a medical function comprising:
   a main body that is elongated;
   a functional conductor which extends in a longitudinal direction of the main body in which the functional conductor and main body are separate elements, or form said main body in which the functional conductor and main body are a single element, and which comprises an inductive section that comprises
      a magnetic flux generation element configured to generate a magnetic flux, and
      an insertion or attachment element configured to accept said magnetic flux generation element surrounding the functional conductor or proximally to said inductive section; and,
      wherein said magnetic flux generation element is magnetically coupled to the functional conductor such that the magnetic flux generated upon a current flux through the functional conductor is counteracted and a current flux density through the functional conductor is thus reduced;
      wherein said magnetic flux generation element comprises multiple sections configured to various frequencies of an external field, and adapted separately to different frequencies; and,
      wherein said magnetic flux generation element is settable to a predetermined active frequency in an implanted state of the implantable element; and
   a mechanical adjustment element configured to change a relative position between the inductive section of the functional conductor and the at least one flux generation section of the magnetic flux generation element.

2. The implantable element according to claim 1, wherein the magnetic flux generation element comprises:
   an inductive conductor section, which is
      incorporated with the main body without interruption of a course of the functional conductor or
      is placed on the main body; and,
   a capacitive element attached thereon to form an LC element.

3. The implantable element according to claim 2, wherein the inductive section of the functional conductor is configured as a primary coil of a transformer, and the inductive conductor section of the magnetic flux generation element is configured as a secondary coil of a transformer.

4. The implantable element according to claim 1, configured as an electrode line comprising:
   at least one electrode;
   an electrode terminal contact on one end of the electrode line;
   wherein the functional conductor connects the at least one electrode to the electrode terminal contact wherein said functional conductor comprises at least one coiled section; and,
   at least one magnetic flux generation section, of the multiple sections, coiled coaxially or corradially with the at least one coiled section of the functional conductor.

5. The implantable element according to claim 4, wherein the magnetic flux generation element comprising multiple flux generation sections, of the multiple sections, are connected one behind another along the functional conductor.

6. The implantable element according to claim 4, wherein the at least one flux generation section of the magnetic flux generation element comprises a conductive coating of the functional conductor, or of said inductive section.

7. The implantable element according to claim 1, configured as a guide wire or catheter or vascular support, wherein the functional conductor has at least one coiled section and the magnetic flux generation element comprises a flux generation section, of the multiple sections, coiled coaxially or corradially with the at least one coiled section of the functional conductor.

8. The implantable element according to claim 1, wherein the magnetic flux generation element comprises a capacitive element, which is embedded in an inner area of the inductive section of the functional conductor or at least partially encloses the inductive section.

9. The implantable element according to claim 8, wherein the capacitive element which is embedded in the inductive section or at least partially encloses said inductive section is formed by two coaxial metal cylinders comprising a dielectric filling.

10. The implantable element according to claim 8, wherein the capacitive element comprises multiple capacitive elements that are situated one behind another along the functional conductor.

11. The implantable element according to claim 1, wherein the multiple sections configured to various frequencies of an external field are configured through implementation of various values of inductance and/or capacitance by dimensioning.

12. The implantable element according to claim 11, wherein the multiple sections of the magnetic flux generation element configured to various frequencies are formed by inductive sections having embedded or enclosing capacitive elements situated one behind another along the functional conductor, which have said various values of inductance and/or capacitance.

13. An electronic implant or cardiac pacemaker or implantable defibrillator comprising:
   a connection element configured to connect to an implantable element wherein said connection element comprises
      a main body that is elongated;
      a functional conductor which extends in a longitudinal direction of the main body in which the functional conductor and main body are separate elements, or form said main body in which the functional conductor and main body are a single element, and which comprises
      an inductive section that comprises
   a magnetic flux generation element configured to generate a magnetic flux, and
      an insertion or attachment element configured to accept said magnetic flux generation element surrounding the functional conductor or proximally to said inductive section;
      wherein said magnetic flux generation element is magnetically coupled to the functional conductor in such a way that the magnetic flux generated upon a current flux through the functional conductor is counteracted and a current flux density through the functional conductor is thus reduced;
      wherein said magnetic flux generation element comprises multiple sections configured to various frequencies of an external field, and adapted separately to different frequencies; and,
      wherein said magnetic flux generation element is settable to a predetermined active frequency in an implanted state of the implantable element;

and/or an integrated magnetic flux generation element configured to generate a magnetic flux surrounding the functional conductor, or said inductive section, which is magnetically coupled to the functional conductor in such a way that the magnetic flux generated upon said current flux through the functional conductor is counteracted and the current flux density through the functional conductor is thus reduced; and a mechanical adjustment element configured to change a relative position between the inductive section of the functional conductor and the at least one flux generation section of the magnetic flux generation element.

14. The implantable electronic implant or cardiac pacemaker or implantable defibrillator according to claim 13, wherein the magnetic flux generation element comprises an inductive conductor section; and wherein the inductive section of the functional conductor is configured as a primary coil of a transformer, and the inductive conductor section of the magnetic flux generation element is configured as a secondary coil of a transformer.

* * * * *